United States Patent [19]

Stern et al.

[11] Patent Number: 5,451,400
[45] Date of Patent: Sep. 19, 1995

[54] NUCOSAL COMPETITIVE EXCLUSION FLORA

[75] Inventors: Norman J. Stern; J. Stan Bailey; Nelson A. Cox, Jr.; Leroy C. Blankenship, all of Athens, Ga.

[73] Assignee: The United States of America as represented by the Secretary of Agriculture, Washington, D.C.

[21] Appl. No.: 358,550

[22] Filed: Dec. 14, 1994

Related U.S. Application Data

[63] Continuation of Ser. No. 31,983, Mar. 16, 1993, abandoned.

[51] Int. Cl.⁶ .............................................. C12N 1/20
[52] U.S. Cl. .................................. 424/933; 424/94.4; 426/2
[58] Field of Search ................... 424/93.3, 93.4; 426/2

[56] References Cited

U.S. PATENT DOCUMENTS 4,335,107  6/1982  Snoeyenbos et al. ............... 424/93.3
4,657,762  4/1987  Mikkola et al. ..................... 424/93.3

FOREIGN PATENT DOCUMENTS 2233343  1/1991  United Kingdom .

OTHER PUBLICATIONS

Difco Manual, 9th ed, 1977, p. 256.
Blanchfield et al., J. Food Prot 47(7):542–545 (1984) Abstract BA78:84561.
Mangels et al., J Clin Microbiol 5(S):505–509 (1977). Abstract BA64:33428.
Nurmi, E. and Rantala, M. *Nature*, vol. 241, pp. 210–211 (1973).
Stern et al., *Avian Diseases*, vol. 32, pp. 330–334 (1988).
Stern et al., *Poultry Science*, vol. 70, pp. 790–795 (1991).
Cox et al., *Poultry Science*, vol. 69: pp. 2809–1812 (1990).
Stern, N., *Poultry Science*, vol. 69, supp. 1, p. 130 (1992).

*Primary Examiner*—Marian C. Knode
*Assistant Examiner*—Jean C. Witz
*Attorney, Agent, or Firm*—M. Howard Silverstein; John Fado; Janelle S. Graeter

[57] ABSTRACT

A preparation effective for reducing colonization by human enteropathogenic bacteria in poultry is prepared from cultures of mucosa-associated flora obtained from ceca of mature birds and is referred to as mucosal competitive exclusion (MCE). The preparation is especially effective for both Salmonella and Campylobacter spp. Administration of the novel MCE preparation to newly-hatched or hatching birds provides substantial protection against both microorganisms and results in the diminished presence of both in processed poultry products.

3 Claims, No Drawings

NUCOSAL COMPETITIVE EXCLUSION FLORA

This application is a continuation of application Ser. No. 08/031,983, filed Mar. 16, 1993, now abandoned.

BACKGROUND OF THE INVENTION

1. Field of the Invention

The consumption of improperly prepared poultry products has resulted in numerous cases of human intestinal diseases. It has long been recognized that Salmonella spp. are causative agents of such diseases, and more recently Campylobacter spp., especially *Campylobacter jejuni*, has also been implicated. Both microorganisms may colonize poultry gastrointestinal tracts without any deleterious effects on the birds, and, although some diseased birds can be detected, asymptomatic carriers can freely spread the microorganisms during production and processing, resulting in further contamination of both live birds and carcasses.

2. Description of the Prior Art

Better control measures are needed to minimize the spread of these and other human enteropathogenic bacteria, and the most promising approach to achieve this end has been to decrease the incidence and level of microorganism colonization in poultry gastrointestinal tracts.

An effective means for decreasing colonization of chickens by Salmonella was described by Nurmi and Rantala (1973) and is known as competitive exclusion (CE). The chicken's indigenous intestinal flora plays a significant role in protecting it against Salmonella colonization, and it was found that preparations of subcultured intestinal contents from mature, healthy chickens conferred protection to young chicks whose microflora had not yet been established. Administration of undefined CE preparations to chicks speeds up the maturation of the gut flora in the newly-hatched birds and also provides a substitute for the natural process of transmission of microflora from the adult hen to its offspring. The cleaned and disinfected facilities of contemporary broiler houses do not provide the naturally-occurring microflora which had been provided by hens in days past. Snoeyenbos et al. (1982) developed a technique designed to reduce salmonellae in poultry where the source of CE microflora was lyophilized fecal droppings which were propogated by anaerobic culture. Mikkola et al. (1987) used intestinal fecal and cecal contents as a source of CE microflora. Treatment with their culture required media to be anaerobic and pH balanced. Neither of these CE treatments addressed *Campylobacter jejuni*.

Since CE was known to be effective against Salmonella, a similar method for the control of Campylobacter was investigated by Stern et al. (1988). It was found, however, that treatment with CE preparations, such as described by Nurmi and Rantala (1973), Snoeyenbos et al. (1982) and Mikkola et al. (1987), did not affect Campylobacter colonization. After treatments with five different CE cultures, colonization was observed after challenge by Campylobacter in 81 of 84 chicks, and 45 of 46 control chicks. Shanker et al. (1990) confirmed these observations (Shanker et al. 1990. *Epidemiol. Infect.*, vol. 104, pp. 101–110).

In a subsequent investigation, compositions of mixtures of Salmonella and Campylobacter were administered to day-old chicks. It was believed that the two microorganisms might compete with or otherwise antagonize each other, thereby reducing both populations (Stern et al., 1991). No competition or antagonistic effect was observed, however.

SUMMARY

A modification of the CE method has now been discovered which has proven effective for the control of both Salmonella and Campylobacter. This modification, mucosal competitive exclusion (MCE), utilizes cultures of mucosa-associated flora obtained from the ceca of mature chickens which are free of Salmonella and other poultry pathogens. A subculture from MCE administered to newly hatched or hatching chicks has been demonstrated to provide substantial protection against both microorganisms. When properly applied, MCE treatment results in the diminished presence of both Salmonella and Campylobacter in poultry production. With diminished intestinal carriage in chickens, there should be a subsequent reduced human health risk.

In accordance with this discovery, it is an object of the invention to provide a novel method of preparing a mucosal competitive exclusion (MCE) composition effective for the protection of poultry against infection by human enteropathogenic bacteria capable of colonizing poultry, including both Salmonella and Campylobacter.

It is also an object of the invention to provide a novel method of treating poultry to prevent the infection and growth of such bacteria in the treated birds.

Other objects and advantages of the invention will become readily apparent from the following description.

DETAILED DESCRIPTION OF THE INVENTION

The novel MCE preparation is an undefined composition and is prepared according to the following method:

(1) remove ceca from Salmonella-free birds and throughly remove any internal materials by washing with medium;

(2) aseptically and in an anaerobic environment, either (a) obtain scrapings from the mucin layer of the washed ceca, or (b) cut a piece from the washed ceca;

(3) suspend scrapings or cecal cutting in anaerobic medium; and (4) incubate in an anaerobic environment for a time sufficient to allow proliferation to occur.

The resulting flora-containing medium may then be sub-cultured and expanded as needed to provide sufficient quantities of the preparation needed for treatment procedures.

Preferably, in step (1) a Salmonella-free bird is killed, the ceca aseptically removed and placed in a sterile petri plate in an oxygen-free environment. The ceca is inverted on a sterile glass rod, and the majority of cecal material is gently removed under sterile conditions and discarded. The remaining cecal content is removed by washing with an appropriate medium. The washing step may utilize any medium effective for the stated purpose, including water. A preferred medium is an anaerobic medium, particularly preferred being pre-reduced anaerobic medium (PRAM).

In step (2), a sterile scalpel may be used to either (a) scrape the mucin layer from the washed ceca or (b) cut out an approximately 1-mm piece from the washed ceca.

In step (3), the mucin layer scrapings of step 2(a) may be suspended in about 1 ml PRAM, followed by inoculation of the suspension into about 5 ml fresh PRAM. Alternatively, the cut piece of ceca from step 2(b) may be placed directly into about 5 ml PRAM.

In step (4), the suspensions may be incubated at about 35° C. to about 37° C. for approximately 48 hours.

Prior to subculture and use, cultures should be assayed for the presence of Salmonella. Any effective conventional isolation technique may be utilized.

To ensure that no Campylobacter is present in the MCE preparations, the cultures may be subcultured for two additional passages in PRAM under the above indicated anaerobic conditions.

To obtain sufficient quantities of MCE for treating large numbers of birds, the cultures may be expanded using conventional culture techniques well known to those of skill in the art (e.g., approximately 1:1000 dilution of stock preparation followed by incubation for about 48 hours).

The efficacy of the cultures may be evaluated by determining the colonization dose-50% ($CD_{50\%}$) or colonization quotient (CQ), as described by Stern et al., 1991, and herein incorporated by reference. The $CD_{50\%}$ number represents the average number of challenge bacteria required to colonize the ceca of one-half the chicks in a particular group (test or control), sampled one week after challenge. The CQ represents the mean $\log_{10}$ number of colonies per gram of cecal material for all animals in a particular group. In addition, a protection factor (PF) may be calculated which represents the ratio of the $CQ_{CONTROL}$ to $CQ_{TEST}$. The $CD_{50\%}$ depends upon the protection afforded by MCE against colonization by the challenge microorganism and is independent of numbers of colonies. Therefore, the higher the $CD_{50\%}$ number, the higher the amount of protection which has been conferred. A CQ, on the other hand, depends on the number of colonies formed by the challenge microorganism within the intestinal tract of the birds. Therefore, a lower CQ number is more desirable. Since the PF is a ratio of control to test number, a higher PF number is an indication of better protection. In the case of Salmonella, a PF of at least 6 is indicative of an effective MCE preparation. For Campylobacter, a 100-fold (or $CQ = 10^2$) protection is the minimum acceptable level. When testing for MCE efficacy, challenge doses of Salmonella and Campylobacter may be administered separately or in mixtures. Since the two microorganisms are known to act independently in the gut (Stern et al., 1991), results obtained from simultaneous challenge with both are equally accurate, and the procedure is significantly more convenient.

Poultry is treated by administering an effective amount of the MCE preparation. Treatment with the MCE cultures may be applied in two stages. In the first part, an effective amount of culture is sprayed on birds when they are 50–75% hatched, followed by completion of the incubation period. In chickens, for example, hatching trays can be removed from the hatching cabinet after the eggs have been incubated in an incubator for about 18 days and in a hatching cabinet for about 2.5 days, and each tray is sprayed so that each hatching chick and/or unhatched egg receives about 0.2 to about 0.3 ml of MCE. The hatching trays are then returned to the hatching cabinet to complete incubation.

For the second part of the treatment, an effective amount of MCE is added to the birds' first drinking water and is left in place until all has been consumed. In chickens, for example, an approximately 1:10 dilution of MCE in 1-gallon drinker jars is placed in a broiler house at a ratio of approximately 1 jar per 200 chicks. The jars are left in place until all the culture has been consumed (approximately four hours), resulting in the consumption of approximately 10 ml diluted MCE solution per chick.

Alternatively, the preparation may be effectively administered by adding freeze-dried or encapsulated preparation to feed, injecting in ovo, spraying directly on chicks after all are pipped, or by administering through the farm water system.

The novel MCE culture and treatment method are effective for all poultry raised for purposes of human consumption which could serve as carriers of the target pathogens. Poultry includes all domestic fowl raised for eggs or meat, such as chickens, turkeys, ducks and geese.

The target pathogens include all human enteropathogenic bacteria capable of colonizing poultry. Of particular interest are Salmonella and Campylobacter species.

The following examples are intended only to further illustrate the invention and are not intended to limit the scope of the invention as defined by the claims.

EXAMPLE 1

Preparation of Mucosal Competitive Exclusion Culture

A fully mature Salmonella-free chicken was killed and the ceca aseptically removed. The specimen was immediately placed in a sterile petri plate within an oxygen-free nitrogen chamber. The ceca was then inverted on a sterile glass rod and the majority of cecal material removed with a sterile pipet tip. The remaining material was washed with PRAM by expressing it in a stream though a sterile needle from a syringe containing the PRAM. The mucin layer was then scraped from the washed cecal material using a sterile scalpel, and the scrapings were suspended in 1.0 ml PRAM. The suspension was drawn into a sterile syringe, then inoculated into a tube containing 5 ml fresh PRAM. The culture was then incubated at 37° C. for 48 hours. The entire procedure was carried out in an oxygen-free environment achieved by passing a constant stream of nitrogen through the culture preparation chamber.

EXAMPLE 2

Test for MCE Efficacy Against Campylobacter

Three to ten one-day-old chicks held in isolation units were gavaged with 0.2 ml MCE preparation, and a similar number of chicks were left untreated as controls. Twenty-four hours to thirty-six hours post-gavage, the chicks were challenged with Campylobacter at dosages ranging as shown in Table 1. At seven days the chicks were sacrificed. The ceca were harvested, the contents plated on medium selective for Campylobacter and incubated microaerobically (5% $O_2$, 10% $CO_2$, 85% $N_2$) at 42° C. for 24 hours. The $CD_{50\%}$ was found by determining at what dosage one-half of the chick ceca were colonized. The CQ was found by determining the number of colonies per gram cecal material harvested from all chicks treated at a particular dosage.

The data presented in Table 1 shows that in three separate tests the protection afforded by MCE treatment was at least 100-fold. In addition, it can also be seen that chicks sacrificed at days 21 and 42 had retained similar levels of protection.

TABLE 1

COLONIZATION DOSE OF *CAMPYLOBACTER JEJUNI* FOR 50% OF CHALLENGED CHICKS

| | | TREATMENT | |
|---|---|---|---|
| TRIAL | CHICK AGE(D) | CONTROL | MCE |
| EXPT 1 | 7 | $10^{2.0}$ | $10^{4.0}$ |
| EXPT 2 | 7 | $<10^{1.0}$ | $10^{4.0}$ |
| EXPT 2 | 21 | $<10^{1.0}$ | $10^{4.0}$ |
| EXPT 3 | 21 | $10^{3.0}$ | $10^{5.0}$ |
| EXPT 4 | 7 | $10^{3.0}$ | $10^{4.0}$ |
| EXPT 4 | 21 | $10^{2.0}$ | $10^{5.0}$ |
| EXPT 4 | 42 | $10^{2.0}$ | $10^{4.0}$ |

The CQ data presented in Table 2 also indicates the same protective capacity. The CQ value for MCE treated chicks are consistently lower than for the controls.

TABLE 2

COLONIZATION QUOTIENT OF *CAMPYLOBACTER JEJUNI* IN CHICKS CHALLENGED WITH CA. $10^3$ CELLS AT 2 DAYS POST-HATCH

| | | TREATMENT | |
|---|---|---|---|
| TRIAL | CHICK AGE (D) | CONTROL | MCE |
| EXPT 1 | 7 | $10^{3.2}$ | $10^{0.3}$ |
| EXPT 2 | 7 | $10^{2.0}$ | 0 |
| EXPT 2 | 21 | $\sim 10^{3.0}$ | $10^{2.2}$ |
| EXPT 3 | 21 | $10^{1.6}$ | $10^{0.5}$ |
| EXPT 4 | 7 | $10^{1.6}$ | $10^{0.5}$ |
| EXPT 4 | 21 | $10^{5.5}$ | 0 |
| EXPT 4 | 42 | $10^{3.8}$ | 0 |

EXAMPLE 3

Test for MCE Efficacy Against Salmonella

Chicks were treated essentially as described in Example 2. After the ceca were harvested, however, cecal material was plated on medium selective for Salmonella and incubated at 37° C. for 24 hours. The CQ values were determined as described for Campylobacter and are presented in Tables 3 and 4 along with the numbers of positives per test group. It can be seen that MCE treatment also conferred considerable protection against colonization by Salmonella.

TABLE 3

EFFICACY TEST AGAINST *SALMONELLA*

| | Challenge level | #Positive/#Tested | CQ |
|---|---|---|---|
| Control | $10^4$ | 9/9 | $10^{2.5}$ |
| Control | $10^6$ | 6/9 | $10^{3.3}$ |
| MCE3 | $10^4$ | 0/10 | 0 |
| MCE3 | $10^6$ | 0/10 | 0 |

TABLE 4

EFFICACY TEST AGAINST *SALMONELLA*

| | Challenge level | #Positive/#Tested | CQ |
|---|---|---|---|
| Control | $10^3$ | 0/15 | 0 |
| Control | $10^5$ | 14/15 | $10^{4.3}$ |
| Control | $10^7$ | 12/15 | $10^{3.5}$ |
| MCE | $10^3$ | 0/15 | 0 |
| MCE | $10^5$ | 4/15 | $10^{0.4}$ |
| MCE | $10^7$ | 3/15 | $10^{0.3}$ |

We claim:

1. A method of preparing a mucosal competitive exclusion composition effective for the protection of poultry against infection by Salmonella and Campylobacter, said method comprising:
   (a) removing ceca from Salmonella-free birds and thoroughly washing with pre-reduced anaerobic medium;
   (b) aseptically and in an anaerobic environment, obtaining scrapings from the mucin layer of said washed ceca;
   (c) suspending said scrapings in pre-reduced anaerobic medium;
   (d) incubating the suspension in an anaerobic environment at about 35° C. to about 37° C. for at least approximately 48 hours; and
   (e) removing a portion of the suspension.
2. The product produced by the method of claim 1.
3. A method of treating poultry to protect against infection by Salmonella and Campylobacter, said method comprising administering an effective amount of the product of claim 2.

* * * * *

UNITED STATES PATENT AND TRADEMARK OFFICE
CERTIFICATE OF CORRECTION

PATENT NO. : 5,451,400
DATED : September 19, 1995
INVENTOR(S) : Norman J. Stern et al It is certified that error appears in the above-indentified patent and that said Letters Patent is hereby corrected as shown below:

Title page, item [54] and column 1, line 2 "NUCOSAL" should read --MUCOSAL--.

Signed and Sealed this

Twenty-eighth Day of November 1995

Attest:

BRUCE LEHMAN

Attesting Officer  Commissioner of Patents and Trademarks